United States Patent
Hu et al.

(10) Patent No.: US 7,968,083 B2
(45) Date of Patent: Jun. 28, 2011

(54) METHODS OF MANUFACTURING DEODORANTS, AND DEODORANTS RESULTING THEREOF

(75) Inventors: Jinlian Hu, Hung Hom (CN); Fang Zeng, Guangzhou (CN); Pei Li, Hung Hom (CN)

(73) Assignee: The Hong Kong Polytechnic University, Hong Kong SAR (CN)

( * ) Notice: Subject to any disclaimer, the term of this patent is extended or adjusted under 35 U.S.C. 154(b) by 2082 days.

(21) Appl. No.: 10/824,645

(22) Filed: Apr. 15, 2004

(65) Prior Publication Data

US 2005/0232880 A1    Oct. 20, 2005

(51) Int. Cl.
*A61K 8/00* (2006.01)
*A61K 8/18* (2006.01)
*A61K 8/02* (2006.01)
*A61Q 15/00* (2006.01)

(52) U.S. Cl. .......................................... 424/65; 424/401
(58) Field of Classification Search .................... 424/65, 424/401
See application file for complete search history.

(56) References Cited

U.S. PATENT DOCUMENTS

| | | | | |
|---|---|---|---|---|
| 3,669,103 | A | 6/1972 | Harper et al. | 128/156 |
| 3,670,731 | A | 6/1972 | Harmon | 128/284 |
| 4,683,258 | A * | 7/1987 | Itoh et al. | 524/434 |
| 5,284,900 | A * | 2/1994 | Izubayashi et al. | 524/492 |
| 5,556,835 | A * | 9/1996 | Inaoka et al. | 512/3 |
| 5,569,364 | A | 10/1996 | Hooper et al. | 204/455 |
| 6,194,375 | B1 * | 2/2001 | Ness et al. | 512/4 |
| 6,303,711 | B1 * | 10/2001 | Sumiya et al. | 526/73 |
| 6,322,665 | B1 * | 11/2001 | Sun et al. | 162/158 |

FOREIGN PATENT DOCUMENTS

| | | |
|---|---|---|
| EP | 0442185 A1 | 8/1991 |
| JP | 7-81206 | 3/1995 |
| JP | 7-189120 | 7/1995 |

* cited by examiner

*Primary Examiner* — Johann R Richter
*Assistant Examiner* — Luke E Karpinski
(74) *Attorney, Agent, or Firm* — Jacobson Holman PLLC

(57) ABSTRACT

This invention provides a deodorant capable of releasing deodorant agents at certain temperatures and having improved adherence to textiles. The deodorant of this invention includes polymer particles formed by reacting a main monomer of (N-substituted alkyl)acrylamide, a functional monomer for bonding the polymer particles to a fibrous substrate, and a cross-linking agent. A deodorant agent is loaded to the polymer particles.

26 Claims, 5 Drawing Sheets

METHODS OF MANUFACTURING DEODORANTS, AND DEODORANTS RESULTING THEREOF

FIELD OF THE INVENTION

This invention relates to methods of manufacturing deodorants, particularly those that may release deodorant agents at specific temperatures.

BACKGROUND OF THE INVENTION

Body odor is generally caused by fatty acids on skin and by malodors from microbial sources. Numerous attempts have been made to control or absorb body odors, like depriving the moisture environment required by microorganisms responsible for body odor, for example by using powders and/or antiperspirants. Some attempts tried to use compounds such as EDTA to inhibit the formation of such fatty acids. Masking body odors with other odors or perfumes may be another alternative, even though perfumes are often inadequate to fully conceal body odors and may be irritating to some users.

Recently there has been a further growing demand for high level deodorizing functions provided in fibrous products such as clothing, household articles, various personal care products and the like. Conventionally methods for providing deodorizing characteristics on fibrous materials are by kneading a deodorant substance into the interior of polymers during synthetic fiber yarn production, for example as described in Japanese patent no. JP-B-7-81206. Alternatively, a deodorizing agent may be fixed to the surfaces of fibers with a binder, for example as described in Japanese patent publication no. JP-A-7-189120. However, for personal care products like sanitary napkin, pantyliner, diaper, incontinence pad, interlabial article, tampon, shoe liner and etc., it may be desirable to provide controlled release of deodorant at a certain temperature, say around 35° C. This may reduce the loss of deodorant substances, which are caused by factors such as evaporation and penetration.

OBJECTS OF THE INVENTION

Therefore, it is an object of this invention to provide a deodorant capable of releasing deodorant agents at certain temperatures and having improved adherence to textiles. As a minimum, it is an object of this invention to provide the public with a useful choice.

SUMMARY OF THE INVENTION

Accordingly, this invention provides a method of manufacturing a deodorant. Firstly, polymer particles are formed by reacting a main monomer of (N-substituted alkyl)acrylamide, a functional monomer for bonding the polymer particles to a fibrous substrate, and a cross-linking agent. A deodorant agent is then loaded to the polymer particles.

Preferably, the main monomer is selected from the group consisting of N-isopropyl acrylamide, N-methylacrylamide, N-ethylacrylamide, N-n-butylacrylamide, N-n-propylacrylamide, N-n-propylmethacrylamide, N-isopropylmethacrylamide, N-ethylmethacrylamide, N-acroylpiperidine, N-methacroylpiperidine, N-pyrolichylmethylacrylamide, N-piperidylmethylacrylamide, and N,N'-diethylacrylamide, and N-isopropylacrylamide. The main monomer may be preferred to be in an amount of 80% to 90% by weight of the polymer particles.

Advantageously, the functional monomer is selected from the group consisting of acrylamide, allyl alcohol, n-(isobutoxymethyl)acrylamide, N-(isobutoxymethyl)methacrylamide, m and p-vinylbenzyl alcohol, cyanomethyl methacrylate, 2-poly(ethyleneoxy)ethyl acrylate, methacryloyloxypolyglycerol, glyceryl methacrylate, 2-hydroxyethyl acrylate, 2-hydroxypropyl acrylate, 2-hydroxypropyl methacrylate, N-vinyl-2-pyrrolidone, p-aminostyrene, aconitic acid, acrylic acid, methacrylic acid, fumaric acid, itaconic acid, maleic acid, 2-methacryloyloxyethylsulfuric acid, sodium salt, pyridinium 2-methacryloyloxyethylsulfate, 3-acrylamidopropane-1-sulfonic acid, potassium salt, p-styrenesulfonic acid, sodium salt, 3methacryloyloxypropane-1-sulfonic acid, sodium salt, 2acrylamido-2-methylpropanesulfonic acid, methacrylic acid, lithium methacrylate, 2-methacryloyloxyethyl 1 sulfonic acid ammonium p-styrenesulfonate, sodium o and p-styrenesulfonate, N-(3-acrylamidopropyl)ammonium methacrylate, N-(2-methacryloyloxyethyl)-N,N,N-trimethylammonium iodide, N-(2-methacryloyloxyethyl)-N,N,N-trimethylammonium p-toluenesulfonate, 1,2-dimethyl-5-vinylpyridinium methosulfate, N-(2-methacryloyloxyethyl)-N,N,N-trimethylammonium bromide, N,N-trimethylammonium fluoride, N-vinylbenzyl-N,N,Ntrimethylammonium chloride, 3-methyl-1-vinylimidazolium methosulfate, N-(3-methacrylamidopropyl)-N-benzyl-N,N-dimethylammonium chloride, and N-(3-methacrylamidopropyl-N,N,N-trimethylammonium chloride. The functional monomer may be preferred to be in an amount of 5% to 15% by weight of the polymer particles.

Preferably, the cross-linking agent is selected from the group consisting of 2-(diethylamino)ethyl acrylate, 2-(dimethylamino)ethyl acrylate, 2-(dimethylamino)ethyl methacrylate, and 2-(diethylamino)ethyl methacrylate, and N,N'-methylenebisacrylamide (BisAAm). The cross-linking agent may be preferred in an amount of 1% to 10% by weight of the polymer particles.

Preferably, the polymer particles have a lower critical solution temperature, and the polymer particles are formed at a temperature above the lower critical solution temperature.

Preferably, the polymer particles are attached to the fibrous substrate by hydrogen-bond.

Alternatively, the polymer particles are attached to the fibrous substrate by a binding agent. Preferably, the binding agent is selected from the group consisting of polyglycols, polycarboxylic acids, polycarboxylates, poly(lactone)s polyols, polyamides, polyamines, polysulfonic acids, polysulfonates, gamma-aminopropyltrialkoxysilanes, gamma-isocyanatopropyltriethoxysilane, vinyl-trialkoxysilanes, glycidoxypropyltrialkoxysilanes and ureidopropyltrialkoxysilanes.

Advantageously, the deodorant agent is selected from the group consisting of C18:1 dioic acid, C18:2 dioic acid, and phenyl compounds. Preferably, the phenyl compound is selected from the group consisting of phenyl alcohols, phenyl acids, and phenyl esters. The phenyl alcohols are further preferred to be selected from the group consisting of benzyl alcohol, 2-hydroxybenzyl alcohol, 2,3-dimethoxybenzyl alcohol, t-butylhydroquinone, pyrocatechol, and 2-amino-4-nitrophenol. The phenyl acids can be selected from the group consisting of gallic acid, benzoic acid, salicylic acid and ferulic acid, while the phenyl esters can be selected from the group consisting of benzyl cinnamate, monoterpene derivatives including geranic acid, sterols including cholesterol, and ergosterol, steroids including testosterone, and androstenedione, flavonoids including naringenin, isosakuranetin, eriodictyol, and genistein, steryl esters including amyrin cinnamate, 2,7-naphthalenediol, oxyquinoline, and cyclodextrins and their derivatives thereof.

Preferably, the deodorant agent is loaded during synthesis of the polymer particles. Alternatively, the deodorant agent is loaded by hydrophobic interaction with the polymer particles.

BRIEF DESCRIPTION OF THE DRAWINGS

Preferred embodiments of the present invention will now be explained by way of example and with reference to the accompanying drawings in which.

DETAILED DESCRIPTION OF THE PREFERRED EMBODIMENT

Figure 1:
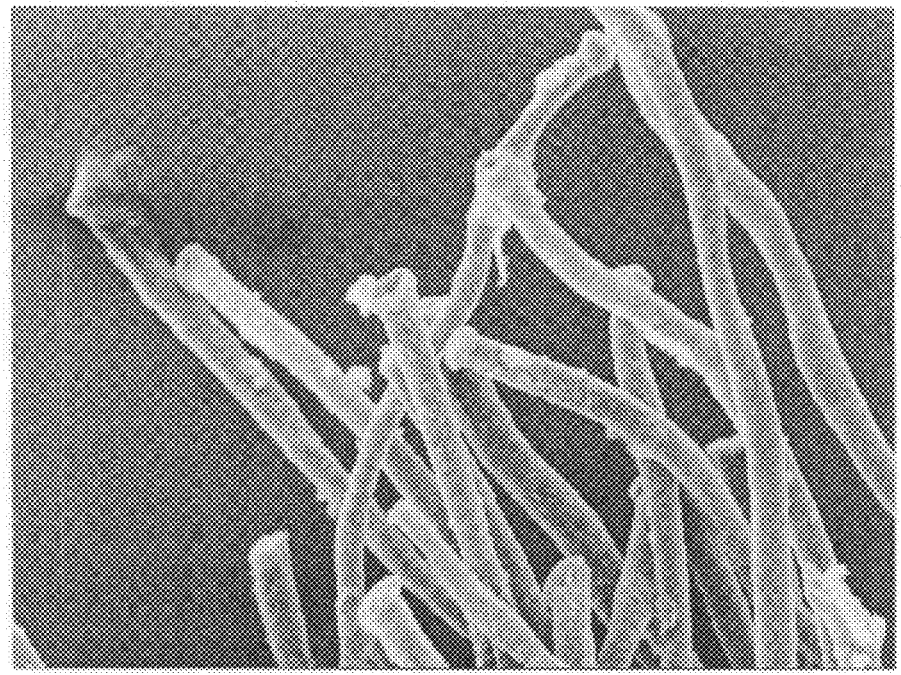
FIG. 1 to 5 shows electromicrographs of the fibrous substrates loaded with the deodorant of this invention.

This invention is now described by way of example in the following paragraphs. Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

The deodorant of this invention is capable of controllably releasing deodorant agents or substances. Such deodorants may be attached to fibrous substrates relatively securely. Of course, the deodorants of this invention may be used alone but one particular application is to be used on fibrous substrates or materials. Generally, the fibrous materials can be woven or non-woven textiles having a width sufficient to form the body-facing surface of the article. These fibrous materials include, but not limited to, cellulose and derivatives, polyester, nylon and silk materials. Further, the fibrous materials can be modified to introduce some functional groups on them to act as the binding site for deodorant microparticles, or the temperature sensitive microgel deodorant.

I. Temperature Sensitive Microgel Deodorant

The temperature sensitive microgel deodorant can be synthesized through precipitation polymerization or inverse emulsion polymerization some vinyl monomers in water. The polymer microgel particles that are used in this invention are copolymers of at least three different monomers:

- about 80 to about 94% by weight of a main monomer;
- about 5 to about 15% by weight of one or more functional monomers; and
- 1 to 10% by weight of a crosslinking monomer having at least two addition polymerizable groups.

The main monomers that can be used in the above methods include, but not limited to, N-isopropyl acrylamide, N-methylacrylamide, N-ethylacrylamide, N-n-butylacrylamide, N-n-propylacrylamide, N-n-propylmethacrylamide, N-isopropylmethacrylamide, N-ethylmethacrylamide, N-acroylpiperidine, N-methacroylpiperidine, N-pyrolichylmethylacrylamide, N-piperidylmethylacrylamide, and N,N'-diethylacrylamide, preferably N-isopropylacrylamide.

The main monomers used in this invention should be those whose polymers have a lower critical solution temperature in water so that temperature sensitive microgels in the form of polymer particles can be prepared by precipitation polymerization. For example, the lower critical solution temperature (LCST) of poly-N-isopropylacrylamide poly(NIPAM) in an aqueous medium is about 32° C. Thus it will be precipitated if the polymerization temperature is above 32° C. during polymerization. Table 1 shows other similar systems in aqueous medium whose LCSTs are known. At LCST, poly (NIPAM) undergoes a reversible phase transition resulting in the collapse of the microgel structure due to the hydrophobic interaction between isopropyl groups in the polymer chain.

TABLE 1

| List of LCSTs of aqueous solution of polymers | |
|---|---|
| Polymer | LCST (° C.) |
| poly (N-methylacrylamide) | 95 |
| poly (N-ethylacrylamide) | 80 |
| poly (N-n-butylacrylamide) | 25 |
| Poly (N-isopropylacrylamide) | 32 |
| poly (N-n-propylacrylamide) | 16-19 |
| poly (N-n-propylmethacrylamide) | 22-29 |
| poly (N-isopropylmethacrylamide) | 40 |
| poly (N-ethylmethacrylamide) | 54-57 |
| poly (N-acroylpiperidine) | 4-6 |
| poly (N-methacroylpiperidine) | 18-42 |
| poly (N-pyrolichylmethylacrylamide) | 53 |
| poly (N-piperidylmethylacrylamide) | 42 |
| poly (N,N'-diethylacrylamide) | 30-32 |

Some functional groups can be incorporated onto the microgels by using specific functional monomers so that the resulting polymer particles can be adhered or bonded to the fibrous substrate. Examples of suitable functional monomers that are useful for making the copolymer microgels used in this invention include, for example, acrylamide, allyl alcohol, n-(isobutoxymethyl)acrylamide, N-(isobutoxymethyl)methacrylamide, m and p-vinylbenzyl alcohol, cyanomethyl methacrylate, 2-poly(ethyleneoxy)ethyl acrylate, methacryloyloxypolyglycerol, glyceryl methacrylate, 2-hydroxyethyl acrylate, 2-hydroxypropyl acrylate, 2-hydroxypropyl methacrylate, N-vinyl-2-pyrrolidone, p-aminostyrene, aconitic acid, acrylic acid, methacrylic acid, fumaric acid, itaconic acid, maleic acid, 2-methacryloyloxyethylsulfuric acid, sodium salt, pyridinium 2-methacryloyloxyethylsulfate, 3-acrylamidopropane-1-sulfonic acid, potassium salt, p-styrenesulfonic acid, sodium salt, 3methacryloyloxypropane-1-sulfonic acid, sodium salt, 2acrylamido-2-methylpropanesulfonic acid, methacrylic acid, sodium salt, lithium methacrylate, 2-methacryloyloxyethyl 1 sulfonic acid ammonium p-styrenesulfonate, and sodium o and p-styrenesulfonate. Examples of suitable cationic monomers include, for example, N-(3-acrylamidopropyl)ammonium methacrylate, N-(2-methacryloyloxyethyl)-N,N,N-trimethylammonium iodide, N-(2-methacryloyloxyethyl)-N,N,N-trimethylammonium p-toluenesulfonate, 1,2-dimethyl-5-vinylpyridinium methosulfate, N-(2-methacryloyloxyethyl)-N,N,N-trimethylammonium bromide, N,N-trimethylammonium fluoride, N-vinylbenzyl-N,N, Ntrimethylammonium chloride, 3-methyl-1-vinylimidazolium methosulfate, N-(3-methacrylamidopropyl)-N-benzyl-N,N-dimethylammonium chloride, and N-(3-methacrylamidopropyl-N,N,N-trimethylammonium chloride. Such hydrophilic monomers are well known in the art and are generally considered to be functional monomers that can be used to provide specific groups on the microgel to act as the binding site for incorporating the microgels onto the fibrous materials.

The polymerization composition should also comprise at least one cross-linking agent, so that the microgel can be formed in the polymerization. Example of suitable crosslinking agents includes 2-(diethylamino)ethyl acrylate, 2-(dimethylamino)ethyl acrylate, 2-(dimethylamino)ethyl methacrylate, and 2-(diethylamino)ethyl methacrylate. A preferred crosslinking agent is N,N'-methylenebisacrylamide (BisAAm).

The suitable initiators for this invention are water-soluble or oil-soluble initiators, which include oxide initiators like persulfates, peroxides and azo-contained compounds, as well as redox initiators, which are known to a person skilled in the art. In this invention, persulfates like ammonium persulfate and potassium persulfate are preferred.

The polymer microgel particles used in this invention can be prepared by emulsifier-free emulsion polymerization (precipitation) processes or inverse suspension polymerization, as described in U.S. Pat. No. 5,569,364, incorporated by reference herein. In a typical precipitation polymerization process, the water is degassed with an inert gas such as argon or nitrogen, to remove oxygen, and a mixture of the monomers are added to the water. The initiator is added and the mixture is heated above the LCST of the corresponding polymer for about 1 to 3 hours. The polymerization is complete when the monomer concentration, which can be monitored, diminishes to nearly zero. The resulting copolymers typically have average diameters (swollen, in water) in the range of about 0.1 to about 2.0 micrometer, often about 0.3 to about 1 micrometer.

The microgel can also be prepared by inverse suspension polymerization, The term "inverse" suspension polymerization is used to imply a heterogeneous polymerization system in which the monomer is readily soluble in water, but only sparingly soluble, if at all, in non-polar liquids. Thus, in the inverse suspension polymerization an aqueous solution of a hydrophilic monomer is dispersed in a continuous hydrophobic medium using a surface-active substance which promotes the formation of water-in-oil emulsions. The polymerization is then initiated with water-soluble initiators. Sorbitan monostearate is a water-in-oil emulsifier which is suitable for this application. The inverse suspension polymerization is as follows. The suspensions are formed by dissolving the emulsifier in o-xylene or a suitable organic medium such as toluene and adding the aqueous monomer solution with stirring. The crude suspensions are homogenized to decrease the average droplet size and increase the emulsion stability. The suspensions are heated with stirring at 40° C. to 70° C. to effect polymerization, depending on the initiator used. The time required for complete conversion varies from a few minutes to several hours. The particles formed by this method can range from 30 nm to 3000 nm, depending on the amount of surfactant added. To purify, the particles are centrifuged several times with deionized water.

II. Binding Microgel Particles onto Fibrous Materials

Traditional hydrogel polymer particles suffer from poor adherence to the substrate if the particles not chemically bound to fibrous substrate securely. Separation of the hydrogel particles from its substrate diminishes the effectiveness of the hydrogel particle. This problem was addressed in European Patent Application 442 185 A1, U.S. Pat. No. 3,669,103 and U.S. Pat. No. 3,670,731, which disclose use of inorganic or organic binder to bind a hydrogel particles a fibrous substrate. In accordance with the present invention, microgel particles are bound to the textile fibers to give the fibers desired properties, in this invention, the controlled release of deodorant upon being heated to a certain temperature. The microgel particles are capable of forming covalent bonds or non-covalent bond such as hydrogen bonds, with the fibrous materials.

Hydrogen bonds can be formed, as discussed above, by particles containing functional groups having oxygen and nitrogen, and/or hydrogen bonding to oxygen or nitrogen. Suitable functional groups may include, but not limited to, hydroxyls, carboxyls, sulfonic acids, sulfonamides, ethers, esters, epoxides, carbonyls, amines, urethanes. Specific examples of natural fibers that contain a hydrogen bonding functionality include chopped silk fibers, wood pulp fibers, bagasse, hemp, jute, bamboo, sisal, cotton, flax, kenaf, and mixtures thereof. Suitable synthetic fibers with hydrogen bonding functionalities include acrylic, polyester, carboxylated polyolefins, rayon and nylon. The hydrogen-bonding functionality is an ester in acrylic fibers and a carboxylic acid in carboxylated polyolefin fibers, an ester in polyester, an amide in nylon, and a hydroxyl in rayon. In this invention, the binders were used to incorporate hydrogel particles onto fibrous materials by forming hydrogen bond.

The binder used in the present invention comprises binder molecules wherein the binder molecules have at least one functional group capable of forming a hydrogen bond with the particles, and at least one functional group capable of forming a hydrogen bond with fibrous material substrate. It should be noted that a binder molecule is not a must for this invention to work, and the fibrous substrate can form hydrogen bond with the polymer particles directly. Both the polymeric or non-polymeric binder can be suitable. The polymeric binder may be selected from the group consisting of polyglycols (especially polyethylene glycol or poly(propyleneglycol), a polycarboxylic acid, a polycarboxylate, a poly (lactone) polyol, such as diols, a polyamide, a polyamine, a polysulfonic acid, a polysulfonate and combinations thereof. The non-polymeric binder is an organic binder, and preferably includes a functional group selected from the group consisting of a carboxyl (for example, carboxylic acids), a carboxylate, a carbonyl (for example, aldehydes), a sulfonic acid, a sulfonate, a phosphoric acid, a phosphate, an amide, an amine, a hydroxyl (such as an alcohol) and combinations thereof.

Alternatively, covalent bonds can be formed by connecting the functional groups on the microgel particles to the functional groups on the fibrous materials with coupling agents. Functional organo silane coupling agents are preferred for use in the present invention. Examples of useful functional organo silane coupling agents include gamma-aminopropyltrialkoxysilanes, gamma-isocyanatopropyltriethoxysilane, vinyl-trialkoxysilanes, glycidoxypropyltrialkoxysilanes and ureidopropyltrialkoxysilanes. Preferred functional organo silane coupling agents include A-187 gamma-glycidoxy-propyltrimethoxysilane, A-174 gamma-methacryloxypropyltrimethoxysilane, A-1100 gamma-aminopropyltriethoxysilane silane coupling agents, A-1108 amino silane coupling agent and A-1160 gamma-ureidopropyltriethoxysilane (each of which are commercially available from OSi Specialties, Inc. of Tarrytown, N.Y.). The organo silane coupling agent can be at least partially hydrolyzed with water prior to application to the fibers, preferably at about a 1:1 stoichiometric ratio or, if desired, applied in unhydrolyzed form. Suitable transition metal coupling agents include titanium, zirconium, yttrium and chromium coupling agents. Suitable titanate coupling agents and zirconate coupling agents are commercially available from Kenrich Petrochemical Company. Suitable chromium complexes are commercially available from E.I. duPont de Nemours of Wilmington, Del. The amino-containing Werner-type coupling agents are complex compounds in which a trivalent nuclear atom such as chromium is coordinated with an organic acid having amino functionality. Other metal chelate and coordinate type coupling agents known to those skilled in the art can be used herein. Moreover, some coupling agents like divinyl sulfone and glutaraldehyde can also be used, these coupling agents are preferable in this invention due to their high reactivity in room temperature.

III. Deodorant Agents

The following is an non-exhaustive list of deodorants that can be use in this invention: dicarboxylic acids, especially unsaturated dicarboxylic acids, e.g. C18:1 dioic acid, and C18:2 dioic acid; phenyl compounds including: phenyl alcohols, e.g. benzyl alcohol, 2-hydroxybenzyl alcohol, 2,3-dimethoxybenzyl alcohol, t-butylhydroquinone, pyrocatechol, and 2-amino-4-nitrophenol; phenyl acids, e.g. gallic acid, benzoic acid, salicylic acid and ferulic acid; phenyl esters, e.g. benzyl cinnamate; monoterpene derivatives, e.g. geranic acid; sterols, e.g. cholesterol, and ergosterol; steroids, e.g. testosterone, and androstenedione; flavonoids, e.g. naringenin, isosakuranetin, eriodictyol, and genistein; steryl esters, e.g. amyrin cinnamate; and 2,7-naphthalenediol, and oxyquinoline; cyclodextrins and their derivatives.

In the present invention, cyclodextrins and derivatives are preferred due to its capability of absorbing a broad spectrum of odors by forming complexes with them. The family of cyclodextrin includes: unsubstituted cyclodextrins containing from six to twelve glucose units, especially, alpha-cyclodextrin, beta-cyclodextrin, gamma-cyclodextrin and/or their derivatives and/or mixtures thereof. The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. Preferred, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof.

Usually the deodorant may be present in an amount ranging from 0.001 to 10% by weight of the composition, preferable from 0.01 to 2%. This range is of course variable and may depend on various factors like the deodorant agent used.

IV. Loading and Controlled Release of Deodorants

The deodorants can be loaded into the polymer particles or microgels either during the synthesis of microgels, or can be absorbed into the microgels bound to the fibrous materials due to hydrophobic interactions between the deodorant and the stationery phase (e.g., the microgels on fibrous materials). While for the controlled release of deodorants, the microgels shrink and at the mean time change their hydrophobicity upon contact with warm body fluid or human skin, thus expel the deodorant.

The following examples will serve to further typify the nature of the invention but should not be construed as a limitation on the scope thereof, which is defined solely by the appended claims.

Example 1

Microgel Preparation by Precipitation Polymerization

As stated above, precipitation polymerization is carried out above the LCST of the corresponding linear polymer. The recipe for the polymerization is given in Table 2:

TABLE 2

Typical recipe for precipitation polymerization using N-isopropylacrylamide:

| Reagent | Amount (g) |
| --- | --- |
| N-isopropylacrylamide(NIPAM) | 4.8 |
| N,N'-methylene-bis-acrylamide | 0.1 |
| Hydroxypropyl acrylate (HPA) | 0.2 |
| Potassium persulfate | 0.2 |
| Deionized water | 200 |

The microgel particles of poly(NIPAM/HPA) were prepared by a single-step precipitation polymerization reaction. The polymerization was undertaken in a 500-liter, round-bottom glass flask, under a nitrogen atmosphere at 70° C. The flask was fitted with a reflux condenser, a stainless steel stirring rod with a Teflon paddle, a thermometer, and a glass nitrogen inlet tube. All of the monomers, cross-linking agent and initiator were charged in one shot into the flask containing 200 g of water. The suspension (total volume of 200 cm$^3$) was stirred 350 rpm throughout the reaction overnight. The cooled microgel dispersion was then filtered through glass wool, followed by six cycles of centrifugation in water at 10,000 rpm for 45 min, to remove any unreacted monomer and ionic species which may be present. The particle size for PNIPAM/HPA microgel thus prepared was about 400 nm in swollen state.

Example 2

Microgel Preparation by Inverse Suspension Polymerization

In inverse emulsion polymerization an aqueous solution of a hydrophilic monomer was dispersed in a continuous hydrophobic oil medium using a surface-active substance to promote the formation of water-in-oil emulsions. The polymerization was then initiated with either oil-soluble or water-soluble initiators. Continuous and gentle agitation is needed to maintain these lattices as colloidal dispersion indefinitely. The recipe for the polymerization is given in Table 3:

TABLE 3

Typical recipe for inverse suspension polymerization using N-isopropyl-acrylamide:

| Reagent | Amount (g) |
| --- | --- |
| N-isopropylmethacrylamide | 20 |
| p-aminostyrene | 0.70 |
| N-(3-acrylamidopropyl)ammonium methacrylate | 0.85 |
| Ammonium persulfate | 0.45 |
| Sodium sulfite | 0.55 |
| Sorbitan monostearate | 2.0 |
| Deionized water | 60 |
| Alpha-cyclodextrin | 1.0 |
| O-xylene | 80 |

In this embodiment, N-isopropylmethacrylamide was used as the main monomer, p-aminostyrene used as functional monomer, N,N'-methylene-bis-acrylamide as a cross-linking agent or the cross-linker, sorbitan monostearate (SMS) was used as an emulsifier. One advantage of this embodiment is that the deodorant can be loaded into the microgel during the polymerization. First the aqueous solution of monomers was prepared by dissolving the monomers, cross-linker, deodorant alpha-cyclodextrin and the initiators in to 60 g of water under high-speed stirring for 20 minutes. The emulsions were then formed by dissolving all SMS in 80 g of o-xylene and adding the aqueous monomer solution with stirring. The crude emulsions are homogenized to decrease the average droplet size and to increase the emulsion stability. Then the temperature is controlled at about 40° C. to initiate the polymerization, which lasted 3 to 4 hrs.

Upon completion of polymerization, the final gel particles can be cleaned by centrifuging several times with deionized water. The gel particles are not monodisperse, however one can filter them to a certain size range, for example, using a 1 μm filter to collect particles less than 1 μm.

Example 3

Figure 2:
Figure 3:
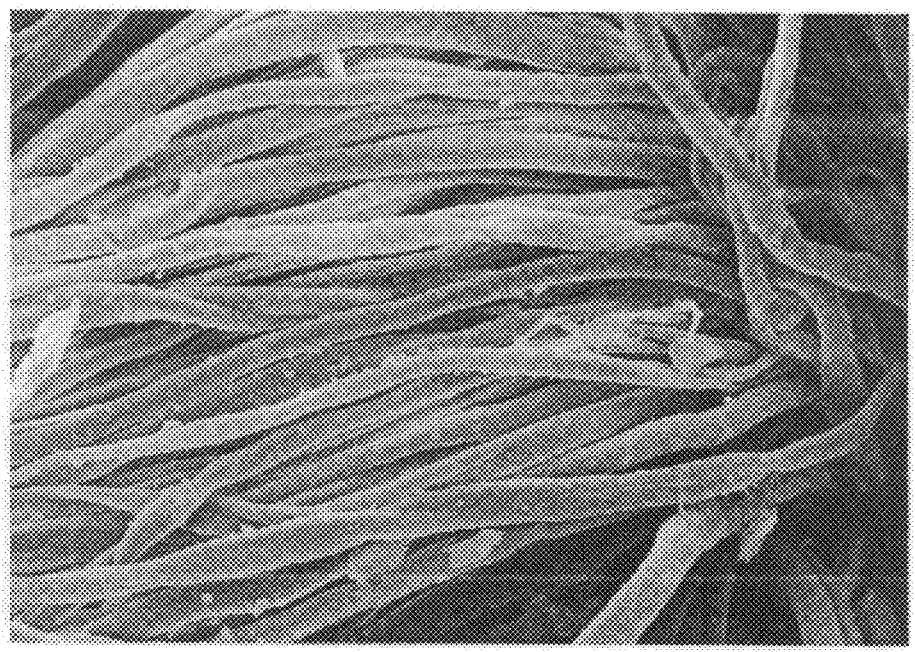
Figure 4:
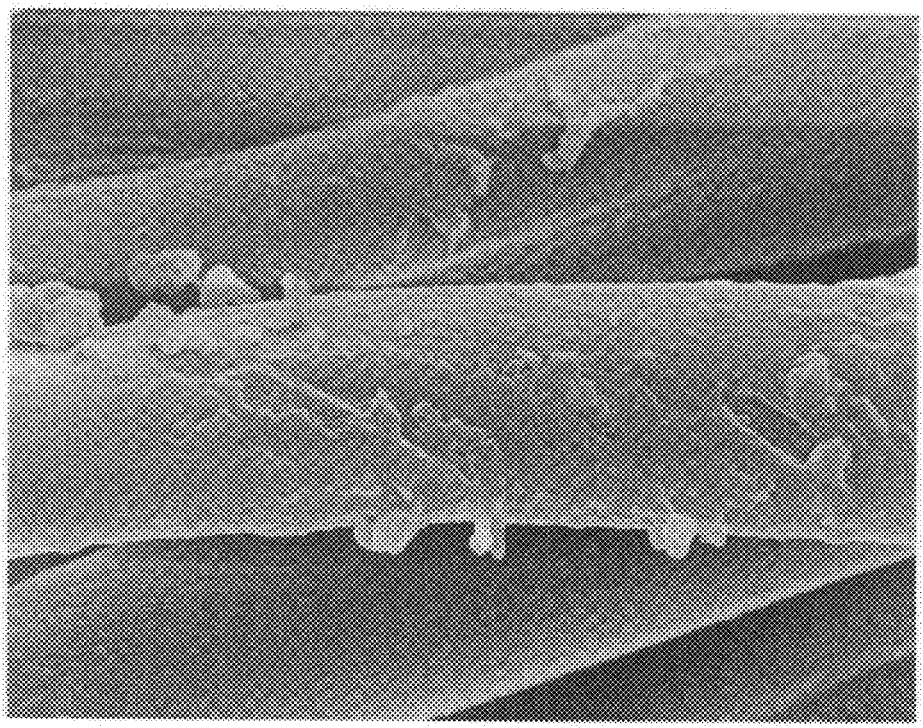
Figure 5:
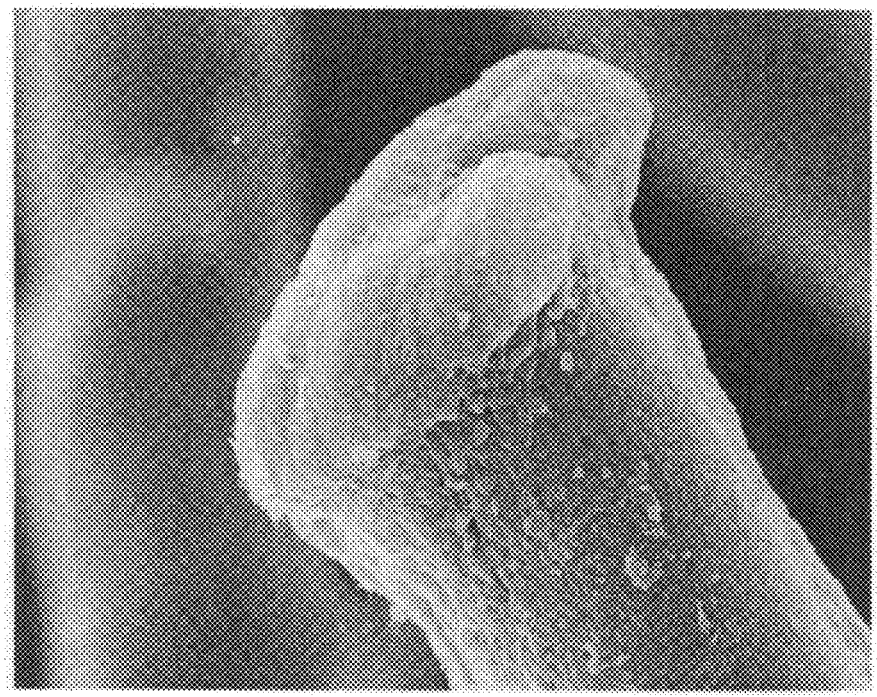
Figure 6:
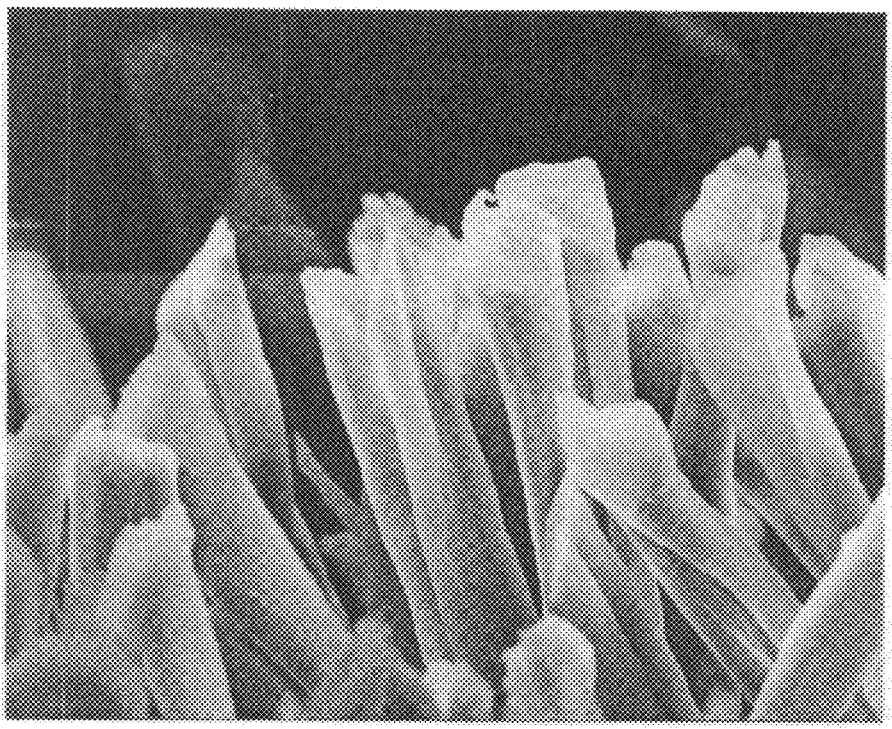
FIGS. 6 to 10 shows electromicrographs of the fibrous substrates without the deodorant of this invention.
Figure 7:
Figure 8:
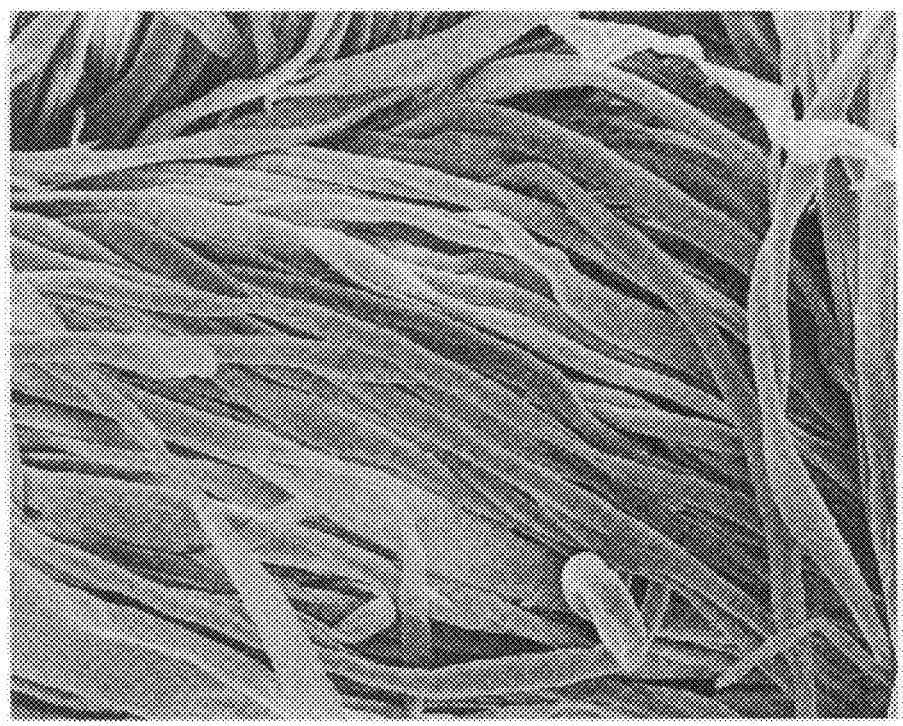
Figure 9:
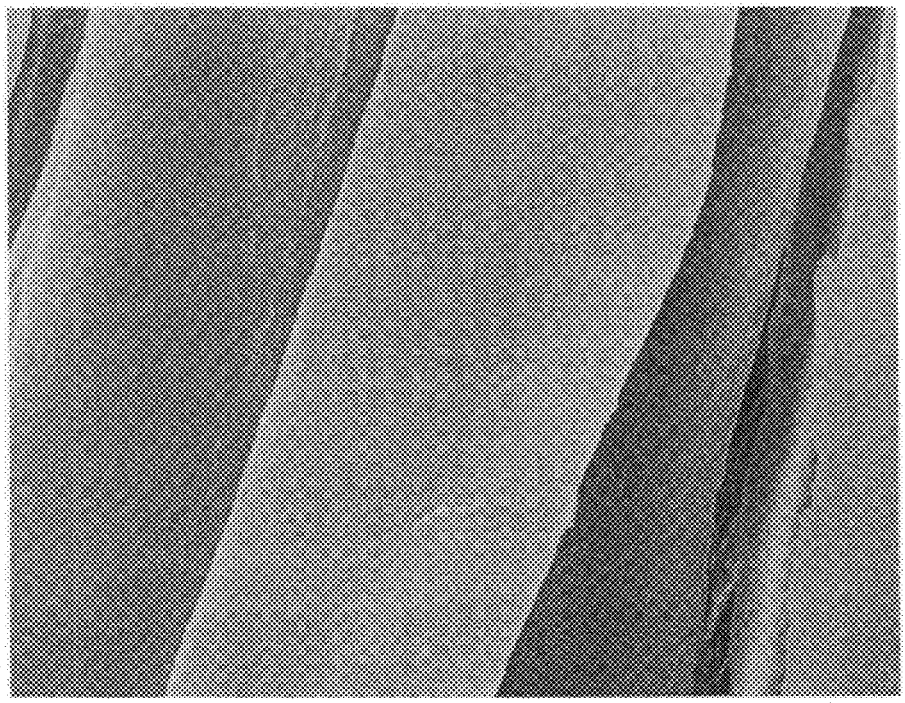
Figure 10:
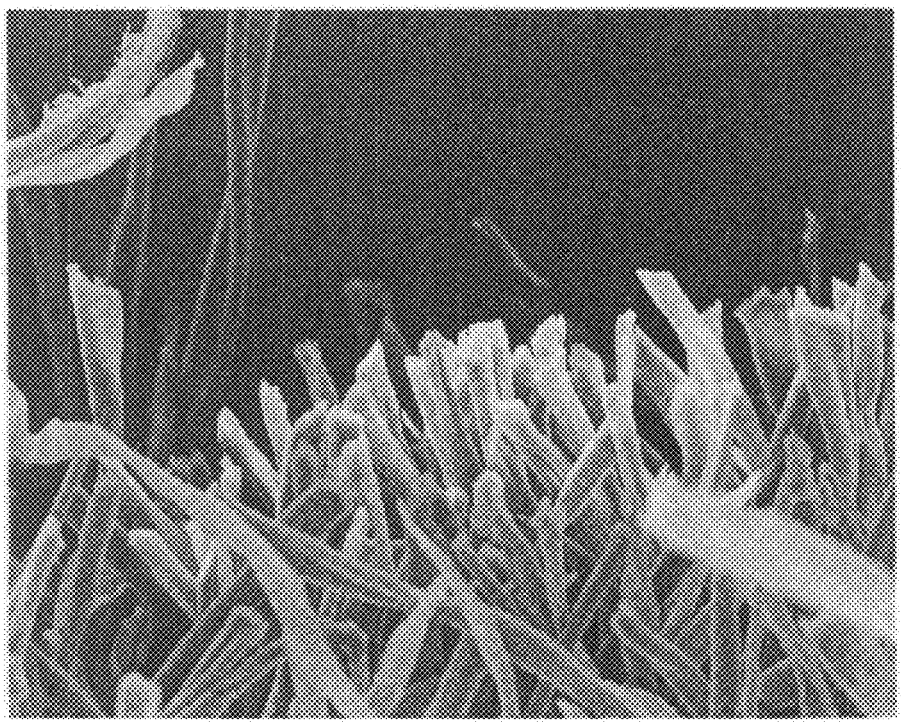

Binding Hydroxyl Group Contained Microgel Particles onto Cotton Textiles 10 grams of divinyl sulfone (coupling agent) was dissolved in 100 g of water at room temperature under stirring, then a 10% of PNIPAM/HPA hydrogel particle dispersions was charged into the solution. Upon stirring for 10 minutes in room temperature, the mixture was sprayed onto the cotton fabric sheet and then the product was vacuumed out, and spread out in a fume hood to dry overnight. The resulting product was examined by scanning electron microscope and revealed particles attached to fibers, and are shown in FIGS. 1 to 10. This example demonstrates that the fibers and particles may be bound together to produce fibrous materials with attached hydrogel particles.

Example 4

Binding of Amino Group Containing Hydrogel Particles onto Jute Fibrous by Using Polymer Binder 300 grams of jute fabric was submerged into 20 grams of a 65% solution of polyacrylic acid (average molecular weight=2,000; commercially available, such as the product supplied by Aldrich chemical company of Milwaukee, Wis.) diluted with 10 ml of deionized water, and then was taken out and be sprayed with 435 grams of 10% dispersion of poly(N-isopropylmethacrylamide/p-aminostyrene)hydrogel particles, the product could then be dried in dry oven under the temperature of 70° C. for 5 hrs. In this embodiment, polyacrylic acid can bind the amino containing particles and hydroxyl containing jute fibers by forming hydrogen bonds with the both.

Example 5

Binding Amino Group Containing Microgel Particles onto Silk Fabric 200 grams of silk fabric was submerged into 100 grams of a 10% solution of glutaraldehyde for 30 minutes, and then was taken out and sprayed with 50 grams of 10% dispersion of poly(N-isopropylmethacrylamide/p-aminostyrene)hydrogel particles, the product can then be dried in fume cupboard under room temperature overnight. In this embodiment, glutaraldehyde can bind the amino containing particles and silk fabric by chemically reacts with the both.

Example 6

Binding Hydroxyl Group Containing Hydrogel Particles onto Nylon Fabric 325 grams of Nylon 6 fiber was mixed with a 500 ml of 10% aqueous solution of glycerin under stirring for 20 minutes at room temperature, and then applied with 100 gram of 10% dispersion of PNIPAM/HPA hydrogel particles. The product was dried in air overnight. In this embodiment, glycerin is advantageous because it tends to penetrate the fibers and soften them in addition to binding the particles to the fibers. However, over time less glycerin is available at the surface of the particles for use in binding particles in the event the glycerin/particle material is stored for long periods prior to use in adhering to fibers (e.g. if reactivation is delayed for several weeks or more). This can be compensated for in part by using higher percentages of glycerin on the particles.

Example 7

Loading of Deodorant into Hydrogel Particles

Not Applicable for Hydrogel Particles Prepared by Inverse Suspension Polymerization, in which the Deodorant can be Loaded During the Reaction 20 grams of fabric materials incorporated with temperature sensitive hydrogel particles was submerged into 300 ml of 10% aqueous solution of alpha-cyclodextrin, the system was then stirred for 5 hrs. The resulting product was taken out and dried in fume cupboard overnight.

Example 8

Controlled Release of Deodorant 20 grams of fabric article containing alpha-cyclodextrin and prepared according to the procedures stated in EXAMPLE 1 through 7 was submerged into 200 ml of deionized water, then the temperature of water was controlled to 25, 27, 29, 30, 31, 32, 33, 34, 35, 36 and 37° C., respectively. At each temperature the fibrous article was maintained in water for 3 hrs under shaking, then 5 ml water was taken from the system for determining the cyclodextrin concentration.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

The invention claimed is:

1. A method of manufacturing a deodorant comprising the steps of:
   forming polymer particles by reacting a main monomer of (N-substituted alkyl)acrylamide, a functional monomer for bonding the polymer particles to a fibrous substrate, a cross-linking agent, and an initiator and
   loading a deodorant agent to the polymer particles,
   wherein the polymer particles have a lower critical solution temperature and the polymer particles are formed at a temperature above the lower critical solution temperature,
   wherein the deodorant agent is selected from the group consisting of C18:1 dioic acid, C18:2 dioic acid, and phenyl compounds, wherein the cross-linking agent is selected from the group consisting of 2-(diethylamino)ethyl acrylate, 2-(dimethylamino)ethyl acrylate, 2-(dimethylamino)ethyl methacrylate, 2-(diethylamino)ethyl methacrylate, and N,N'-methylenebisacrylamide (BisAAm), and wherein the main monomer is present at an amount of 80% to 90% by weight of the polymer particles, the functional monomer is present at an amount of 5% to 15% by weight of the polymer particles, and the cross-linking agent is present at an amount of 1% to 10% by weight of the polymer particles.

2. The method of claim 1, wherein the main monomer is selected from the group consisting of N-isopropyl acrylamide, N-methylacrylamide, N-ethylacrylamide, N-n-butylacrylamide, N-n-propylacrylamide, N-n-propylmethacrylamide, N-isopropylmethacrylamide, N-ethylmethacrylamide, N-acroylpiperidine, N-methacroylpiperidine, N-pyrolichylmethylacrylamide, N-piperidylmethylacrylamide, and N,N'-diethylacrylamide, and N-isopropylacrylamide.

3. The method of claim 1, wherein the functional monomer is selected from the group consisting of acrylamide, allyl alcohol, n-(isobutoxymethyl)acrylamide, N-(isobutoxymethyl)methacrylamide, m and p-vinylbenzyl alcohol, cyanomethyl methacrylate, 2-poly(ethyleneoxy)ethyl acrylate, methacryloyloxypolyglycerol, glyceryl methacrylate, 2-hydroxyethyl acrylate, 2-hydroxypropyl acrylate, 2-hydroxypropyl methacrylate, N-vinyl-2-pyrrolidone, p-aminostyrene, aconitic acid, acrylic acid, methacrylic acid, fumaric acid, itaconic acid, maleic acid, 2-methacryloyloxyethylsulfuric acid, sodium salt, pyridinium 2-methacryloyloxyethylsulfate, 3-acrylamidopropane-1-sulfonic acid, potassium salt, p-styrenesulfonic acid, sodium salt, 3-methacryloyloxypropane-1-sulfonic acid sodium salt, 2-acrylamido-2-methylpropanesulfonic acid, methacrylic acid, lithium methacrylate, 2-methacryloyloxyethyl 1 sulfonic acid ammonium p-styrenesulfonate, sodium o and p-styrenesulfonate, N-(3-acrylamidopropyl)ammonium methacrylate, N-(2-methacryloyloxyethyl)-N,N,N-trimethylammonium iodide, N-(2-methacryloyloxyethyl)-N,N,N-trimethylammonium p-toluenesulfonate, 1,2-dimethyl-5-vinylpyridinium methosulfate, N-(2-methacryloyloxyethyl)-N,N,N-trimethylammonium bromide, N,N-trimethylammonium fluoride, N-vinylbenzyl-N,N,N-trimethylammonium chloride, 3-methyl-1-vinylimidazolium methosulfate, N-(3-methacrylamidopropyl)-N-benzyl-N,N-dimethylammonium chloride, and N-(3-methacrylamidopropyl-N,N,N-trimethylammonium chloride.

4. The method of claim 1, wherein the polymer particles are attached to the fibrous substrate by hydrogen-bond.

5. The method of claim 1, wherein the polymer particles are attached to the fibrous substrate by a binding agent.

6. The method of claim 5, wherein the binding agent is selected from the group consisting of polyglycols, polycarboxylic acids, polycarboxylates, poly(lactone)s polyols, polyamides, polyamines, polysulfonic acids, polysulfonates, gamma-aminopropyltrialkoxysilanes, gamma-isocyanatopropyltriethoxysilane, vinyl-trialkoxysilanes, glycidoxypropyltrialkoxysilanes, glutaraldehyde, and ureidopropyltrialkoxysilanes.

7. The method of claim 1, wherein the phenyl compound is selected from the group consisting of phenyl alcohols, phenyl acids, and phenyl esters.

8. The method of claim 7, wherein the phenyl alcohols are selected from the group consisting of benzyl alcohol, 2-hydroxybenzyl alcohol, 2,3-dimethoxybenzyl alcohol, t-butylhydroquinone, pyrocatechol, and 2-amino-4-nitrophenol.

9. The method of claim 7, wherein the phenyl acids are selected from the group consisting of gallic acid, benzoic acid, salicylic acid and ferulic acid.

10. The method of claim 7, wherein the phenyl esters are selected from the group consisting of benzyl cinnamate, monoterpene derivatives including geranic acid, sterols including cholesterol, and ergosterol, steroids including testosterone, and androstenedione, flavonoids including naringenin, isosakuranetin, eriodictyol, and genistein, steryl esters including amyrin cinnamate, 2,7-naphthalenediol, oxyquinoline, and cyclodextrins and their derivatives thereof.

11. The method of claim 1, wherein the deodorant agent is loaded during synthesis of the polymer particles.

12. The method of claim 1, wherein the deodorant agent is loaded by hydrophobic interaction with the polymer particles.

13. The method of claim 1, wherein the initiator is selected from the group consisting of persulfates, peroxides, azo-contained compounds and redox initiators.

14. A method of manufacturing a deodorant including comprising the steps of:
forming polymer particles by reacting a main monomer of (N-substituted alkyl)acrylamido, a functional monomer for bonding the polymer particles to a fibrous substrate, a cross linking agent, an initiator, and a surface-active substance and
loading a deodorant agent to the polymer particles,
wherein the deodorant agent is selected from the group consisting of C18:1 dioic acid, C18:2 dioic acid, and phenyl compounds,
wherein the cross-linking agent is selected from the group consisting of 2-(diethylamino)ethyl acrylate, 2-(dimethylamino)ethyl acrylate, 2-(dimethylamino)ethyl methacrylate, 2-(diethylamino)ethyl methacrylate, and N,N'-methylenebisacrylamide (BisAAm), and
wherein the main monomer is present at an amount of 80% to 90% by weight of the polymer particles, the functional monomer is present at an amount of 5% to 15% by weight of the polymer particles, and the cross-linking agent is present at an amount of 1% to 10% by weight of the polymer particles.

15. The method of claim 14, wherein the main monomer is selected from the group consisting of N-isopropyl acrylamido, N-methylacrylamide, N-ethylacrylamide, N-n-butylacrylamide, N-n-propylacrylamide, N-n-propylmethacrylamide, N-isopropylmethacrylamide, N-ethylmethacrylamide, N-acroylpiperidine, N-methacroylpiperidine, N-pyrolichylmethylacrylamide, N-piperidylmethylacrylamide, and N,N'-diethylacrylamide, and N-isopropylacrylamide.

16. The method of claim 14, wherein the functional monomer is selected from the group consisting of acrylamido, allyl alcohol, n-(isobutoxymethyl)acrylamido, N-(isobutoxymethyl)methacrylamide, m and p-vinylbenzyl alcohol, cyanomethyl methacrylate, 2-poly(ethyleneoxy)ethyl acrylate, methacryloyloxypolyglycerol, glyceryl methacrylate, 2-hydroxyethyl acrylate, 2-hydroxypropyl acrylate, 2-hydroxypropyl methacrylate, N-vinyl-2-pyrrolidone, p-aminostyrene, aconitic acid, acrylic acid, methacrylic acid, fumaric acid, itaconic acid, maleic acid, 2-methacryloyloxyethylsulfuric acid, sodium salt, pyridinium 2-methacryloyloxyethylsulfate, 3-acrylamidopropane-1-sulfonic acid, potassium salt, p-styrenesulfonic acid, sodium salt, 3-methacryloyloxypropane-1-sulfonic acid, sodium salt, 2-acrylamido-2-methylpropanesulfonic acid, methacrylic acid, lithium methacrylate, 2-methacryloyloxyethyl 1 sulfonic acid ammonium p-styrenesulfonate, sodium o and p-styrenesulfonate, N-(3-acrylamidopropyl)ammonium methacrylate, N-(2-methacryloyloxyethyl)-N,N,N-trimethylammonium iodide, N-(2-dimethyl-5-vinylpyridinium methosulfate, N-(2methacryloyloxyethyl)-N,N,N-trimethylammonium bromide, N,N-trimethylammonium fluoride, N-vinylbenzyl-N,N,Ntrimethylammonium chloride, 3-methyl-1-vinylimidazolium methosulfate, N-(3-methacrylamidopropyl)-benzyl-N,N-dimethylammonium chloride, and N-(3-methacrylamidopropyl-N,N,N-trimethylammonium chloride.

17. The method of claim 14, wherein the polymer particles are attached to the fibrous substrate by hydrogen-bond.

18. The method of claim 14, wherein the polymer particles are attached to the fibrous substrate by a binding agent.

19. The method of claim 18, wherein the binding agent is selected from the group consisting of polyglycols, polycarboxylic acids, polycarboxylates, poly(lactone)s polyols, polyamides, polyamines, polysulfonic acids, polysulfonates, gamma-aminopropyltrialkoxysilanes, gamma-isocyanatopropyltriethoxysilane, vinyl-trialkoxysilanes, glycidoxypropyltrialkoxysilanes, glutaraldehyde and ureidopropyltrialkoxysilanes.

20. The method of claim 14, wherein the phenyl compound is selected from the group consisting of phenyl alcohols, phenyl acids, and phenyl esters.

21. The method of claim 20, wherein the phenyl alcohols are selected from the group consisting of benzyl alcohol, 2-hydroxy benzyl alcohol, 2,3-dimethoxybenzyl alcohol, t-butylhydroquinone, pyrocatechol, and 2-amino-4-nitrophenol.

22. The method of claim 20, wherein the phenyl acids are selected from the group consisting of gallic acid, benzoic acid, salicylic acid and ferulic acid.

23. The method of claim 20, wherein the phenyl esters are selected from the group consisting of benzyl cinnamate, monoterpene derivatives including geranic acid, sterols including cholesterol and ergosterol, steroids including testosterone, and androstenedione, flavonoids including naringenin, isosakuranetin, eriodictyol, and genistein, steryl esters including amyrin cinnamate, 2,7-naphthalenediol, oxyquinoline, and cyclodextrins and their derivatives thereof.

24. The method of claim 14, wherein the deodorant agent is loaded during synthesis of the polymer particles.

25. The method of claim 14, wherein the deodorant agent is loaded by hydrophobic interaction with the polymer particles.

26. The method of claim 14, wherein the initiator is selected from the group consisting of persulfates, peroxides, azo-contained compounds and redox initiators.

* * * * *